(12) United States Patent
Sun (10) Patent No.: US 11,596,656 B2
(45) Date of Patent: Mar. 7, 2023

(54) STEM CELL-PRODUCED MICROVESICLES FOR TREATING TENDON PATHOLOGIES

(71) Applicant: ALBERT EINSTEIN COLLEGE OF MEDICINE, Bronx, NY (US)

(72) Inventor: Hui B. Sun, Chappaqua, NY (US)

(73) Assignee: ALBERT EINSTEIN COLLEGE OF MEDICINE, Bronx, NY (US)

( * ) Notice: Subject to any disclaimer, the term of this patent is extended or adjusted under 35 U.S.C. 154(b) by 805 days.

(21) Appl. No.: 16/327,402

(22) PCT Filed: Aug. 21, 2017

(86) PCT No.: PCT/US2017/047731
§ 371 (c)(1),
(2) Date: Feb. 22, 2019

(87) PCT Pub. No.: WO2018/039100
PCT Pub. Date: Mar. 1, 2018

(65) Prior Publication Data
US 2021/0322482 A1   Oct. 21, 2021

Related U.S. Application Data

(60) Provisional application No. 62/378,392, filed on Aug. 23, 2016.

(51) Int. Cl.
*A61K 35/28* (2015.01)
*C12N 5/077* (2010.01)
*C12N 5/0775* (2010.01)

(52) U.S. Cl.
CPC .............. *A61K 35/28* (2013.01); *C12N 5/066* (2013.01); *C12N 5/0668* (2013.01); *C12N 2533/50* (2013.01)

(58) Field of Classification Search
None
See application file for complete search history.

(56) References Cited

U.S. PATENT DOCUMENTS

| | | | |
|---|---|---|---|
| 2016/0184363 A1 | 6/2016 | Badiavas et al. | |
| 2018/0177828 A1* | 6/2018 | Ludlow | A61K 8/14 |

FOREIGN PATENT DOCUMENTS

WO   2015179227 A1   11/2015

OTHER PUBLICATIONS

Abels et al, Cell Mol Neurobiol, 2016, 36:301-312. (Year: 2016).*
Dai et al, World Journal of Stem Cells, 2019, 11(9): 677-692. (Year: 2019).*
Lange-Consiglio et al, Stem Cells and Development, 2013, 22(22): 3015-3024. (Year: 2013).*
Lange-Consiglio et al, Stem Cells and Development, 2016 (epub: Feb. 2016), 25(8): 610-621. (Year: 2016).*
Urbanelli et al, International Journal of Molecular Sciences, 2016, 17, 1408 (13 pages) (Year: 2016).*
PCT International Search Report and Written Opinion dated Jan. 29, 2018 in connection with PCT International Patent Application No. PCT/US2017/47731.
Tetta, C et al., The role of microvesicles derived from mesenchymal stem cells in tissue regeneration; a dream for tendon repair? Muscles, Ligaments and Tendons Journal. Oct. 16, 2012, vol. 2, No. 3; pp. 212-221.
Abbah, S et al., Assessment of stem cell carriers for tendon tissue engineering in pre-clinical models. Stem Cell Research & Therapy. 2014, vol. 5, No. 2, 9 pages.
Bony, C et al., Adipose Mesenchymal Stem Cells Isolated after Manual or Water-jet-Assisted Liposuction Display Similar Properties. Frontiers of Immunology. Jan. 18, 2016, vol. 6, Article 655; pp. 1-8.
Dragovic, R et al., Isolation of syncytiotrophoblast microvesicles and exosomes and theircharacterisation by multicolour flow cytometry and fluorescence Nanoparticle Tracking Analysis. Methods. Oct. 1, 2015, Epub Apr. 3, 2015, vol. 87; pp. 64-74.
Yuan, H et al., Mechanical property and biological performance of electrospun silk fibroin-polycaprolactone scaffolds with aligned fibers. 2016, Epub Dec. 29, 2015, vol. 27, No. 3; pp. 263-275.

* cited by examiner

*Primary Examiner* — Allison M Fox
(74) *Attorney, Agent, or Firm* — Fox Rothschild LLP

(57) ABSTRACT

Microvesicles produced by stem cells grown on a silk scaffold for enhancing stem cell self-renewal/proliferation and promoting tenogenesis in damaged tendons, and their use in tendon wound repair and tendinopathy treatment. Also provided are compositions containing the microvesicles and devices for obtaining them.

15 Claims, 8 Drawing Sheets

STEM CELL-PRODUCED MICROVESICLES FOR TREATING TENDON PATHOLOGIES

CROSS-REFERENCE TO RELATED APPLICATIONS

This application is a U.S. national stage entry under 35 U.S.C. § 371 of PCT International Patent Application No. PCT/US2017/047731, filed Aug. 21, 2017, which claims benefit of U.S. Provisional Application No. 62/378,392, filed Aug. 23, 2016, the contents of each of which are incorporated herein by reference into the subject application.

BACKGROUND OF THE INVENTION

The disclosures of all references and all patents, patent application publications and books referred to herein are hereby incorporated by reference in their entirety into the subject application to more fully describe the art to which the subject invention pertains.

It takes a long time for a tendon injury to heal, even where it is possible. In most cases, the ruptured tendon does not heal, but forms scar tissue at the injury site. The impaired healing leads to the wounded tendon having impaired mechanical properties and reduced function, and often requires revision surgery. In addition, tendinopathies (chronic tendon degenerative disorders) are also associated with tendon pain and impaired function. Tendinopathy in most cases is due to tendon overload which leads to microscopic collagen fiber failure and a failed healing response, often resulting in tendon rupture. There is currently no cure for tendinopathy.

The present invention address the need for improved tendon rupture and tendinopathy treatments.

SUMMARY OF THE INVENTION

The present invention can enhance self-renewal of the resident stem cells in tendons, and modify the impaired local stem/progenitor cell fate and function to promote tenogenesis and tendon regeneration to improve the disease condition and its associated pam.

A method is provided of treating a damaged tendon in a mammalian subject comprising administering to the subject an amount of microvesicles derived from mammalian mesenchymal stem cells effective to treat a damaged tendon.

Also provided is a method of reducing scar formation in a damaged tendon in a mammalian subject comprising administering to the subject an amount of microvesicles derived from mammalian mesenchymal stem cells effective to treat reduce scar formation.

Also provided is a method of accelerating healing of a damaged tendon in a mammalian subject comprising administering to the subject an amount of microvesicles derived from mammalian mesenchymal stem cells effective to accelerate healing of a damaged tendon.

Also provided is a method of enhancing tenogenesis in a damaged tendon in a mammalian subject comprising administering to the subject an amount of microvesicles derived from mammalian mesenchymal stem cells effective to enhance tenogenesis.

Also provided is a pharmaceutical composition for treating a damaged tendon comprising a sterile pharmaceutically acceptable carrier and an amount of purified microvesicles derived from mammalian mesenchymal stem cells.

Also provided is a method of producing microvesicles derived from mammalian mesenchymal stem cells comprising obtaining adipose-derived stem cells from a mammalian subject by a cannula; placing the adipose-derived stem cells into a sterile culture system comprising a scaffold of longitudinal fibers under tension and under conditions permitting growth of the adipose-derived stem cells on the scaffold of longitudinal fibers; and recovering microvesicles secreted from the cultured adipose-derived stem cells under sterile conditions.

Also provided is a device comprising a 3D scaffold of plurality of fibers substantially aligned in a parallel manner along their longitudinal axes and held under at least 15N of tension in a longitudinal direction of the fibers.

Additional objects of the invention will be apparent from the description which follows.

BRIEF DESCRIPTION OF THE DRAWINGS

FIG. 2A-2G. Therapeutic effect of Micro-vesicles-S injection in overuse-induced tendinopathy in rats. The animals were subjected to overuse treadmill running for 6 weeks. At two weeks after the start of treadmill running, rats were injected with Micro-vesicles-S [MV-S], Microvesicles-C [MV-C], or placebo [P]. The animals maintained in cages served as a naive controls. Histology/immunohistochemistry, mechanical property testing, and pain behavior assessment were carried out in the animals at the end of the experiment. Compared to placebo and exosome control-treated rats, Micro-vesicles-S-treated tendinopathy rats had tendons with (2A) collagen-fiber alignment similar to naive controls, as shown in H&E stained histology sections. The images were representative at sites most susceptible to tendinopathy, at the bone-tendon insertion and midsubstance site of tendon. The improved cellular alignment was supported by quantification of (2B) cell alignment and (2C) cell shape. A comparable reduction in (2D) cleaved collagen and an (2E) increase in collagen I/III were detected in Micro-vesicles-S-treated tendinopathy rats and naive controls, compared to control treatments. (2F) Micro-vesicles-S-treated tendinopathy rats traveled a longer distance in an open field within a 10 minute measurement. (2G) Supraspinatus tendons from Micro-vesicles-S-treated tendinopathy rats exhibited higher maximum load and maximum stress. *p<0.05, one-way ANOVA with Tukey post-hoc test.

DETAILED DESCRIPTION OF THE INVENTION

This invention is based on the discovery that microvesicles produced by stem cells under specific conditions, such as growing on a novel silk scaffold, enhance stem cell self-renewal/proliferation and promotes tenogenesis in vitro, and exert therapeutic effects on tendon wound repair and tendinopathy in vivo.

Mesenchymal stem cells ("MSC", e.g. adipose-derived MSC, bone-marrow-derived MSC, bursa-derived MSC, tendon stem/progenitor cells) at passage 0 (P0) to P2 are cultured on a novel silk rope-like scaffold, which results in the cells to differentiate towards the tenogenic lineage. Within a special window of time, these cells produce and extracellularly secrete microvesicles. This microvesicles can modulate stem cells by enhancing their self-renewal/proliferation and by promoting tenogenesis and accelerate wound or disease healing. The microvesicles can be made by autologous cells so as to provide an autologous therapy for tendon injuries and tendinopathy. In an embodiment, microvesicles are collected from cultured MSC obtained from fat tissue from a subject, e.g. an athlete, or an active and/or aged individuals who is at high risk for, or suffering from, a tendon injury or tendinopathy. In an embodiment the microvesicles are banked before injury and available for administration via, for example, local injection into the wounded or diseased tendon site of the patient when the injury or disease occurs.

A method is provided of treating a damaged tendon in a mammalian subject comprising administering to the subject an amount of microvesicles derived from mammalian mesenchymal stem cells effective to treat a damaged tendon.

As used herein, microvesicles "derived from" or "isolated from" mammalian mesenchymal stem cells are microvesicles made by mammalian mesenchymal stem cells and then obtained. Such microvesicles are usually secreted extracellularly by the cells and are collected from, for example, a culture medium in which the mammalian mesenchymal stem cells are present.

As used herein "treating" a damaged tendon means ameliorating one or more signs or symptoms of tendon damage. For example, amelioration of damaged tendon tissue structure disruption by restoration (full or partial) of tendon cellular and matrix composition, amelioration of damaged tendon mechanical and functional performance by restoration (full or partial) mechanical properties including strength and elasticity of tendon tissue, amelioration of damaged tendon pain, are each examples of treating a damaged tendon.

Also provided is a method of reducing scar formation in a damaged or "repaired" tendon tissue in a mammalian subject comprising administering to the subject an amount of microvesicles derived from mammalian mesenchymal stem cells effective to reduce scar formation. Scar formation or fibrosis in tendon results of non- or incomplete tendon repair or regeneration of damaged tendon tissues. Scar tissues are composites with fibroblasts instead of tenocytes, which produce non-tendon like matrix components with much weaker mechanical property and often lead to re-injury. As used herein "reducing scar formation" in a damaged tendon means ameliorating one or more signs or symptoms of scar formation. For example, reducing the extent of scar formation in a tendon as compared to the extent of scar formation in an equivalent untreated damaged tendon.

Also provided is a method of accelerating healing of a damaged tendon in a mammalian subject comprising administering to the subject an amount of microvesicles derived from mammalian mesenchymal stem cells effective to accelerate healing of a damaged tendon. As used herein "accelerating healing" of a damaged tendon means increasing the rate of healing of a damaged tendon as compared to the rate of healing in an equivalent untreated damaged tendon or reducing the time taken to achieve a predetermined point in the healing process as compared to the time taken to achieve the same predetermined point in an equivalent untreated damaged tendon.

Also provided is a method of enhancing tenogenesis in a damaged tendon in a mammalian subject comprising administering to the subject an amount of microvesicles derived from mammalian mesenchymal stem cells effective to enhance tenogenesis. As used herein "enhancing tenogenesis" in a damaged tendon means increasing the rate and/or amount of tenogenesis in a damaged tendon as compared to the rate and/or amount of tenogenesis, respectively, in an equivalent untreated damaged tendon.

In an embodiment of the methods, the microvesicles have been secreted from mesenchymal stem cells from sources including, but not limited to unless specified, bone marrow, adipose tissue and various tendon tissues. MSCs derived from tendon tissues such as human rotator cuff, and long head of biceps, can be isolated based on plastic adhesion in culture and are phenotypically characterized by flow cytometry with cell surface markers with CD90+, CD146+, CD 44+ and CD34−, CD117−, CD18, CD45−.

In an embodiment of the methods, the mesenchymal stem cells have been cultured on a specifically defined silk scaffold prior to the microvesicles being derived from the mesenchymal stem cells.

In an embodiment of the methods, the mesenchymal stem cells within passages (P)l to P3 following passage 0, which is derived from the cell population isolated via enzymatic digestion of human tissue specimen such as tendon and based on plastic adherence in cell culture have been cultured on a silk scaffold.

In an embodiment of the methods, the mesenchymal stem cells (MSC) are adipose-derived MSC, bone marrow-derived MSC, bursa-derived MSC, or are tendon progenitor cells.

In an embodiment of the methods, the mesenchymal stem cells (MSC) are from the same species as the subject. In an embodiment of the methods, the mesenchymal stem cells (MSC) are from the same subject that is being treated.

In an embodiment of the methods, the damaged tendon is damaged as a result of a tendinopathy. In an embodiment of the methods, the damaged tendon is damaged as a result of physical injury to the tendon. In an embodiment of the methods, the damaged tendon is a ruptured tendon.

In an embodiment the tendon has been treated conservatively with rest, analgesia (such as non-steroidal anti-inflammatory drugs), physiotherapy, and/or surgery repair. For example, for proximal biceps tendon rupture, patients may benefit from non-steroidal anti-inflammatory drugs and physiotherapy, while early surgical repair yields the best results for complete quadriceps tendon ruptures. However, surgery must be performed early in order to avoid scarring of the biceps. With delayed treatment, the biceps may be attached to the *brachialis*.

In an embodiment of the methods, the amount of microvesicles is administered locally into the tendon. In an embodiment of the methods, the amount of microvesicles is administered by injection.

In an embodiment of the methods, the amount of microvesicles has been cryopreserved prior to administration. In an embodiment of the methods, the amount of microvesicles has been cryopreserved below −50° C. In an embodiment of the methods, the amount of microvesicles has been cryopreserved below −75° C. In an embodiment of the methods, the amount of microvesicles has been cryopreserved at −80° C. or below.

In an embodiment of the methods the microvesicles can be administered a plurality of times over a series of time. For example, microvesicles in 0.9% NaCl is administered via injection to the wounded tendon, weekly or used as a single dose treatment.

In one embodiment where microvesicles are being administered, an effective amount is a single administered dose. In one embodiment where microvesicles are being administered, an effective amount will be administered over a series of individual doses.

In an embodiment, the routes of administration is local, e.g. by direct injection. For example, the microvesicles (e.g. naked or in a carrier) can be injected directly into the damaged tendon. Other embodiments of the routes of administration encompassed by the methods of the invention include, but are not limited to, each of the following individual routes, and any subset thereof, auricular, buccal, conjunctival, cutaneous, subcutaneous, endocervical, endosinusial, endotracheal, enteral, epidural, via hemodialysis, interstitial, intraabdominal, intraamniotic, intra-arterial, intra-articular, intrabiliary, intrabronchial, intrabursal, intracardiac, intracartilaginous, intracaudal, intracavernous, intracavitary, intracerebral, intracisternal, intracorneal, intracoronary, intradermal, intradiscal, intraductal, intraepidermal, intraesophagus, intragastric, intravaginal, intragingival, intraileal, intraluminal, intralesional, intralymphatic, intramedullary, intrameningeal, intramuscular, intraocular, intraovarian, intraepicardial, intraperitoneal, intrapleural, intraprostatic, intrapulmonary, intrasinal, intraspinal, intrasynovial, intratendinous, intratesticular, intrathecal, intrathoracic, intratubular, intratumor, intratympanic, intrauterine, intravascular, intravenous, intraventricular, intravesical, intravitreal, laryngeal, nasal, nasogastric, ophthalmic, oral, oropharyngeal, parenteral, percutaneous, periarticular, peridural, rectal, inhalationally, retrobulbar, subarachnoid, subconjuctival, sublingual, submucosal, topically, transdermal, transmucosal, transplacental, transtracheal, ureteral, uretheral, and vaginal administration.

Preferred administration is direct, local administration. In an embodiment, the administration is injection into the tendon. In an embodiment, the administration is injection into the subject within up to 2 cm from the tendon.

In an embodiment, the mammalian subject is a human.

Also provided is a pharmaceutical composition for treating a damaged tendon comprising a sterile pharmaceutically acceptable carrier and an amount of purified microvesicles derived from mammalian mesenchymal stem cells. In an embodiment, the pharmaceutically acceptable carrier comprises a buffered saline. In an embodiment, the pharmaceutically acceptable carrier comprises phosphate-buffered saline (PBS), optionally containing 1 mM EGCG.

Also provided is a method of producing microvesicles derived from mammalian mesenchymal stem cells comprising obtaining adipose-derived stem cells from a mammalian subject by a cannula; placing the adipose-derived stem cells into a sterile culture system comprising a scaffold of longitudinal fibers under tension and under conditions permitting growth of the adipose-derived stem cells on the scaffold of longitudinal fibers; and recovering microvesicles secreted from the cultured adipose-derived stem cells under sterile conditions.

In an embodiment, recovering the microvesicles comprises obtaining culture medium conditioned by the cultured adipose-derived stem cells and ultracentrifuging the conditioned medium under sterile conditions so as to obtain a pellet comprising the microvesicles. In an embodiment, the culture medium is a serum-free medium. In an embodiment, the method further comprises aliquoting the microvesicles for therapeutic use. In an embodiment, the method further comprises freezing the microvesicles for future use. In an embodiment, the ultracentrifuging comprises 1) 300×g, for 5-15 mins; 2) 2000×g, for 5-15 mins; 3) 10,000×g, for 25-35 mins; 4) 100,000×g, for 65-75 mins, with the supernatant being collected after each step, and then washing the pellet (e.g. in phosphate buffered saline (PBS)) an ultracentrifuging once more (100,000×g, for 65-75 mins), to yield the microvesicles. In an embodiment, the microvesicles are isolated by differential ultracentrifugation as follows, with the supernatant being collected after every step: 1) 300×g, 10 minute; 2) 2000×g, 10 minute; 3) 10,000×g, 30 minute; 4) 100,000×g, 70 min. The resulting pellet is washed in PBS, and subjected to one more centrifugation step (100,000×g, 70 min), which yields the microvesicles.

In an embodiment, the microvesicles obtained have an average diameter of 40 nm-100 nm as measured by negative staining transmission electron microscopy.

In an embodiment, the longitudinal fibers are silk fibers. In an embodiment, longitudinal fibers are substantially aligned in a parallel manner along their longitudinal axes and held under at least 15N of tension in a longitudinal direction of the fibers.

Also provided is a device comprising a 3D scaffold of plurality of fibers substantially aligned in a parallel manner along their longitudinal axes and held under at least 16.5N to 19.8N of tension in a longitudinal direction of the fibers.

In an embodiment, the fibers are held under at least 16.5N to 19.8 of tension in a longitudinal direction of the fibers. In an embodiment, the fibers have an average diameter of 11 uM to 15 uM. In an embodiment, the 3D scaffold is contained within a sterile container.

In an embodiment, the device further comprises an amount of mammalian mesenchymal stem cells adhered to or growing along the fibers. In an embodiment, the silk fibers are made of Raw *Bombyx mori* 20122 density silk fiber with chemical modification (Maharam et al. 2015, Bone Research, 3, 15015). The fibers also can be made of other biodegradable and cell growth-friendly surfaces with similar physical properties (such as 11 uM to 15 uM diameter, under 16.5N to 19.8 tension).

All combinations of the various elements described herein are within the scope of the invention unless otherwise indicated herein or otherwise clearly contradicted by context.

This invention will be better understood from the Experimental Details, which follow. However, one skilled in the art will readily appreciate that the specific methods and results discussed are merely illustrative of the invention as described more fully in the claims that follow thereafter.

Experimental Results

Introduction

Unlike current concepts and techniques of stem cell-based therapies, the therapeutic treatment disclosed herein uses microvesicles secreted by stem cells, but not the stem cells themselves. Thus, different from cell-based therapy, there are no live-cell-related hurdles or concerns during product production, storage, transportation, and administration. In particular, this product can be cryopreserved (for example at −80° C. or in liquid nitrogen) for years. One-time production of the microvesicles can be used for multiple treatments. If desired, the microvesicles can even be made while an individual is healthy and stored for later use. These unique microvesicles are produced when stem cells grow on a scaffold and are reprogrammed through physical means. There are no special exogenous chemicals or genetic modifications required to reprograms the cells. Furthermore, the microvesicles can be produced by stem cells which are derived from the subject's own tissues such as fat, bone marrow, and bursa, which are all easy to obtain with no harm, and easy to administer without immune-rejection concerns to the subject.

Examples

I. Exogenous micro-vesicles derived from MSCs grown on a novel scaffold enhances TSPC tenogenic gene expression in vitro: Human primary mesenchymal stem cells (105 cells), such as tendon stem/progenitor cells (TSPCs as an example of MSCs), isolated from the biceps tendon of patients undergoing shoulder replacement surgery (37, 42, 59 y.o.) were cultured on a novel scaffold or regular 2D culture. After 2 days of culture, 2 ml of the 4 ml of conditioned medium was harvested and the micro-vesicles within the medium were collected by ultracentrifugation. Micro-vesicles isolated from the conditioned medium of MSCs grown on the novel scaffold are termed: "Micro-vesicles-S". Micro-vesicles isolated from the conditioned medium of MSCs grown in 2D culture are termed: "Micro-vesicles-C".

TSPCs cultured with exogenous Micro-vesicles-S (10 μg/ml) resulted in the following gene expression profile changes in TSPCs: I) increased expression of tenogenic markers scleraxis (Sex) and tenomodulin (Tnmd) (Fig IA), 2) decreased expression of stem cell markers Oct-4 and Nst (FIG. IB), chondrogenesis marker Sox9 (Fig IC), and adipogenesis markers PPARy and LPL (Fig ID), compared to Micro-vesicles-C or vehicle control (cell culture media). Micro-vesicles-S isolated from a 69 y.o. patient exhibited a similar effect as Micro-vesicles-S from the 37-59 y.o. patients (data not shown).

II. Micro-vesicles-S exerts therapeutic efficacy in an overuse-induced tendinopathy rat model: The potential efficacy of Micro-vesicles-S for treating tendinopathy was tested using the overuse-induced tendinopathy model in rats. Micro-vesicles-S or Micro-vesicles-C (20 μg in 10 μl phosphate buffered saline [PBS]) produced by TSPCs from a 69 y.o. patient were injected into the supraspinatus tendons of adult nude rats (5-6 months-old, Charles River) two weeks after starting a total 6-week overuse-induced tendinopathy protocol (100 decline treadmill running for 17 m/min, 1 hour/day, 5 days a week). Other control animals included a placebo (injected with PBS) and naive (normal cage activity without injection). Four weeks after injection, the animals were sacrificed and the supraspinatus tendons were harvested and subjected to immunohistochemistry and mechanical property testing.

Figure 1A:
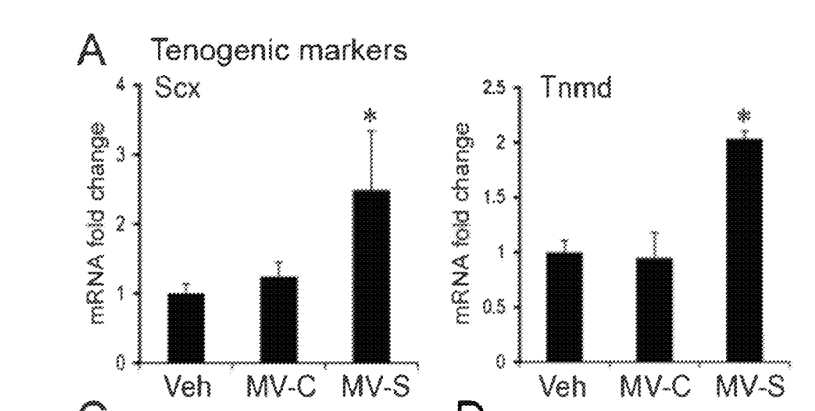
FIG. 1A-1D. Gene expression profile analysis of microvesicles (IA) Gene expression profile that indicates TSPCs treated with Micro-vesicles-S exhibit increased expression of tendon markers ((IA) Sex, Tnmd) and reduced levels of stem cell ((1B) Oct-4, Nst), chondrogenesis ((1C) Sox9), and adipogenesis markers ((1D) PPARy, LPL), with no change in osteogenic marker (Runx, not shown). Scale bar=100 nm. Veh: Vehicle, MV-C: Micro-vesicles-C, MV-S: Micro-vesicles-S. Results represent triplicates of TSPCs treated with micro-vesicles from 37, 42, or 59 y.o. patients.
Figure 1B:
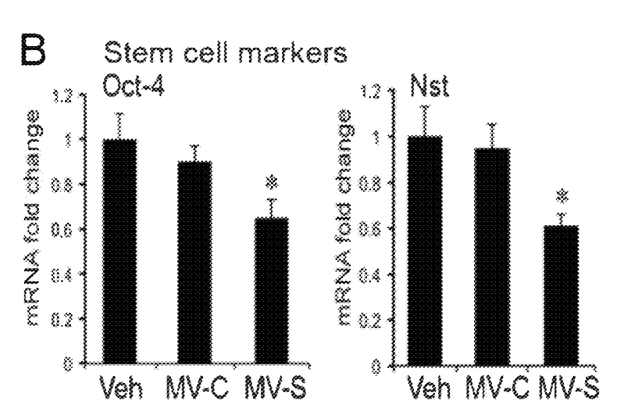
Figure 1C:
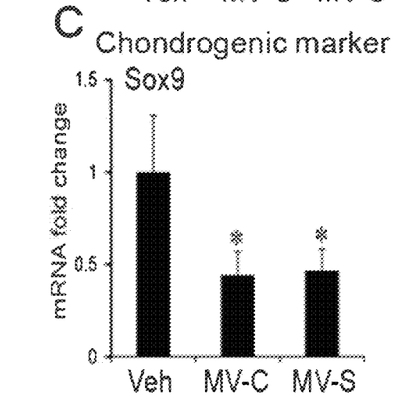
Figure 1D:
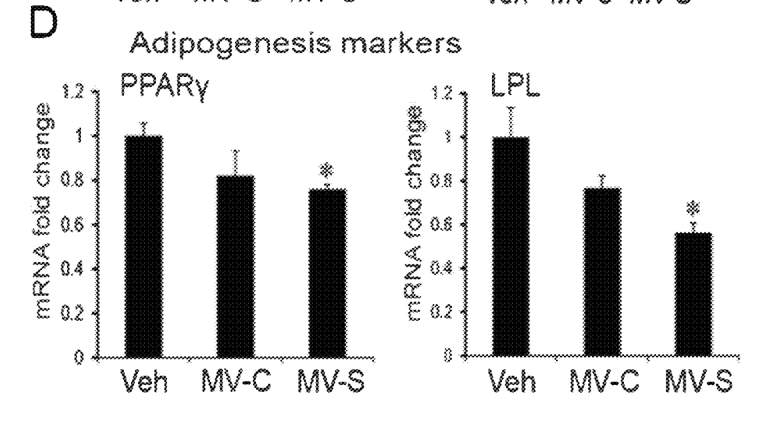
Figure 2A:
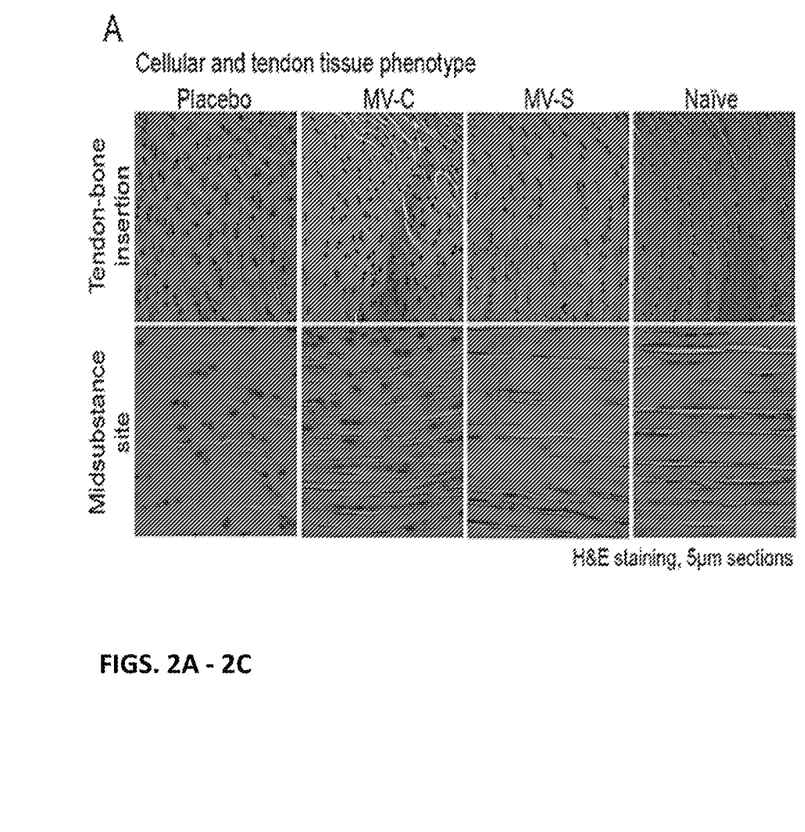
Figure 2B:
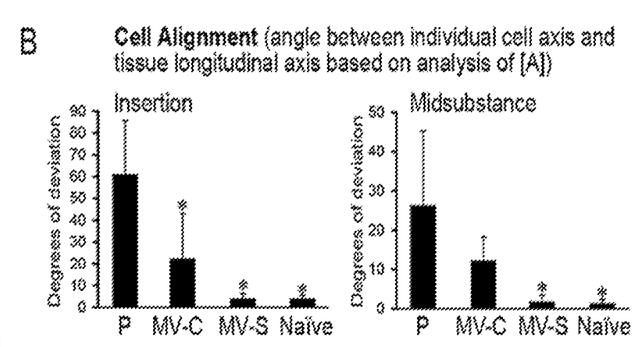
Figure 2C:
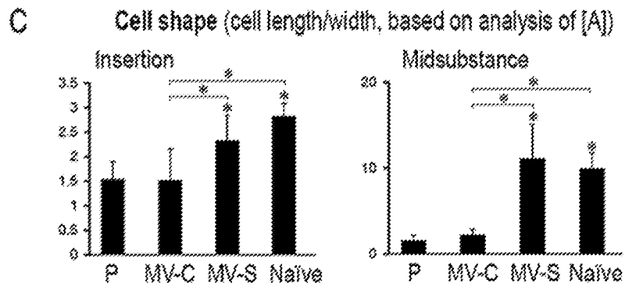
Figure 2D:
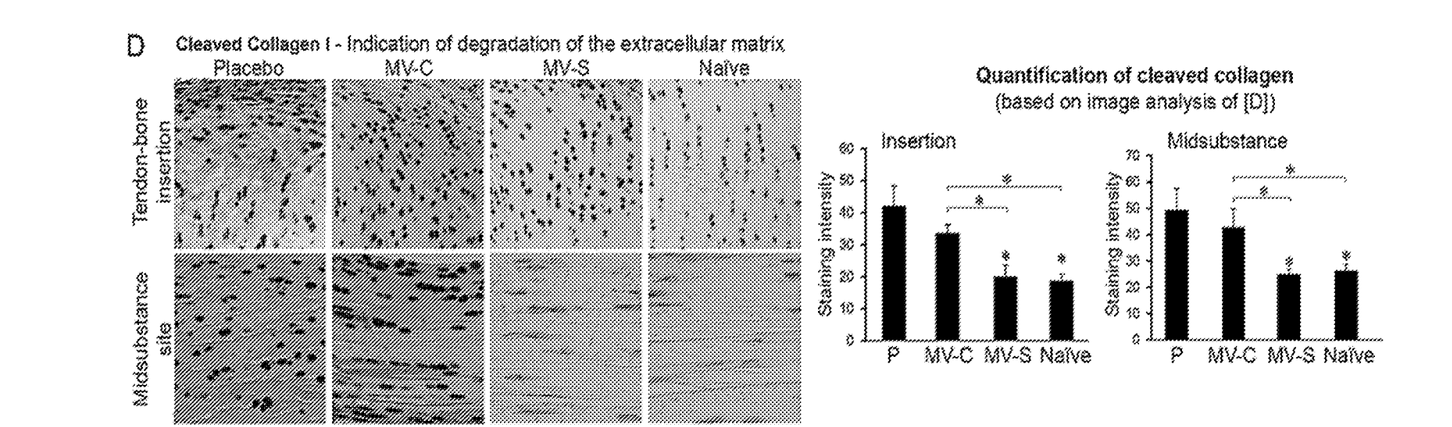
Figure 2E:
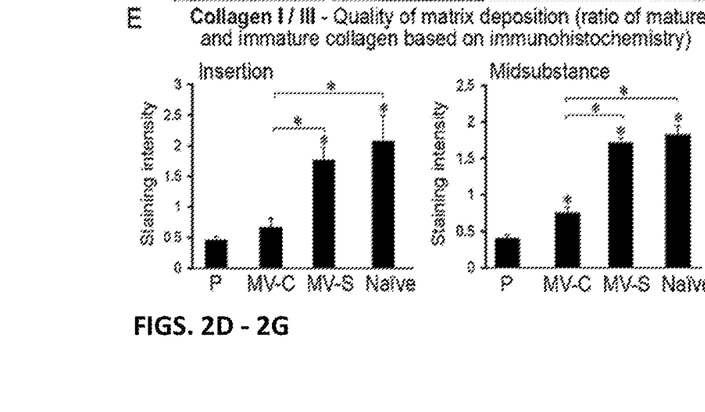
Figure 2F:
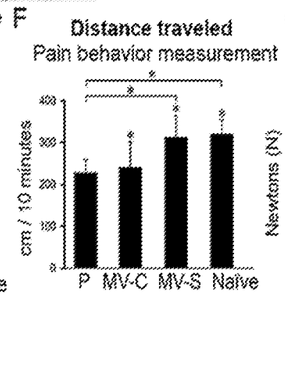
Figure 2G:
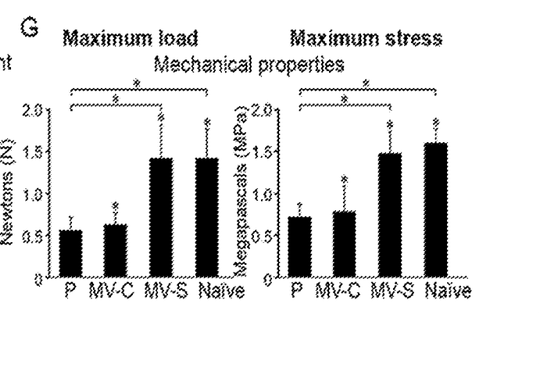

In contrast to placebo and Micro-vesicles-C, the diseased Achilles tendons in rats treated with Micro-vesicles-S exhibited tissue morphology with cell alignment and cell shape similar to that in naive controls as revealed in H&E staining (FIG. 2A), and quantitatively characterized by cell alignment (angle between individual cell axis and tissue longitudinal axis) (FIG. 2B) and cellular shape (cell length I cell width) (FIG. 2C). The diseased Achilles tendons in rats treated with Micro-vesicles-S also exhibited a comparable reduction in cleavage of collagen type I (FIG. 2D), the predominant collagen in native mature tendons, increased intensity of type I collagen (Col I), decreased intensity of Col III, a collagen subtype often associated with scar or immature tendon (FIG. 2E), and a higher number of cells expressing Sex and Tnmd (not shown). The Micro-vesicles-S group was not statistically different from naive animals (p>0.05). Furthermore, Micro-vesicles-S-treated tendinopathy rats exhibited less pain as suggested by an increased total distance traveled in an open field assay (FIG. 2F), and had tendons with stronger mechanical properties (FIG. 2G). These results are consistent with the efficacy of Micro-vesicles-S produced from MSCs of young and middle-aged groups (37, 42, 59 y.o.) based on preliminary studies (not shown).

III. MSC Culture

Figure 3A:
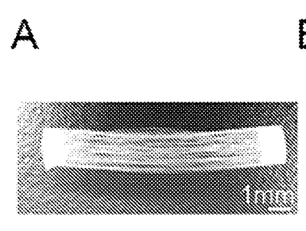
FIG. 3A-3C. MSC attachment after culture on a novel silk scaffold. (3A) Image of scaffold. (3B) Scanning electron microscope image of scaffold. (3C) Immunocytochemistry image of MSCs grown on a silk scaffold for 7 days (blue=DAPI, green=D-actin).
Figure 3B:
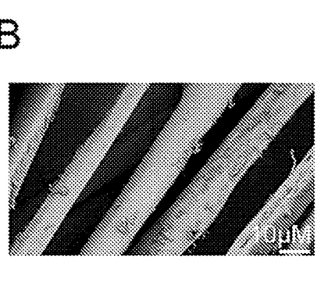
Figure 3C:
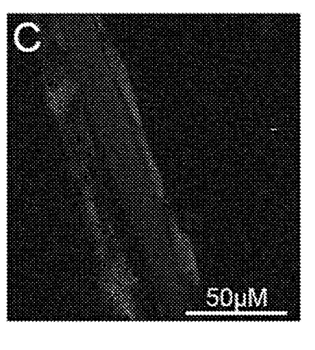

1. MSCs cultured on the novel scaffold elongate along the scaffold fibers. The custom-made silk scaffold (L×W×D, 30 mm×1 mm×1 mm) consists of well-aligned silk fibers held in 19.6N of tension. This scaffold allowed the MSCs to attach and elongate along the fibers, remain viable, and differentiate on the fibers without any additional inductive stimulus. FIG. 3A shows an image of the custom-made parallel-fiber scaffold, and FIG. 3B is a scanning electron microscope image of the scaffold. Seven days post seeding, the C3H10T-1/2 MSCs were able to attach to the scaffold and aligned along the scaffold fibers (FIG. 3C).

Figure 4A:
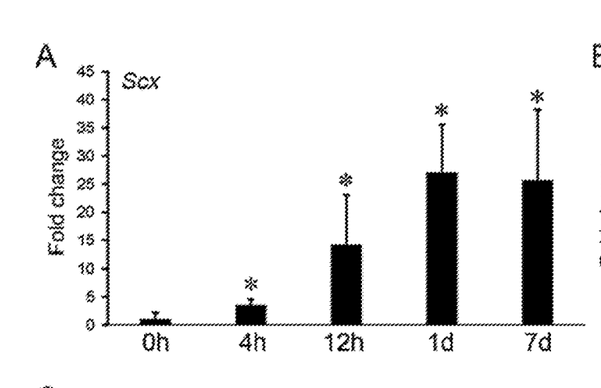
FIG. 4A-4D. MSC differentiation toward tenocytes on rope-like silk scaffold. (4A) Relative mRNA expression of Sex at 0, 4, and 12 h, and 1 day and 7 days after seeding MSCs onto the silk scaffold. (4B) Relative mRNA expression levels of Sex, Tnmd, Nst, Oct4, Sox9, Col2al, Runx2, and Alp in MSCs grown on silk-coated plates or silk scaffolds at 7 days after MSCs were seeded. (4C) Immunocytochemistry staining (blue=DAPI, red=Sex or Tnmd) and (4D) western blot of Sex and Tnmd in cells that were seeded on silk-coated plates and silk scaffolds. Data represent three independent experiments per assay. *P<0.05 compared to MSCs grown on silk-coated plates. Scale bar=50 μm.
Figure 4B:
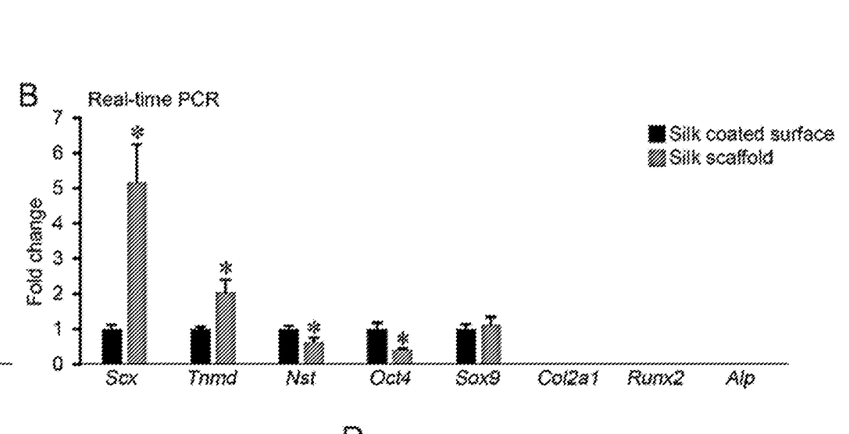
Figure 4C:
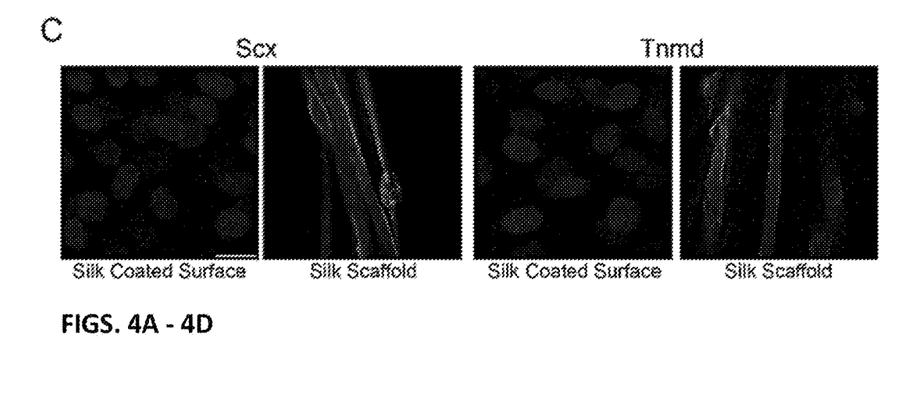
Figure 4D:
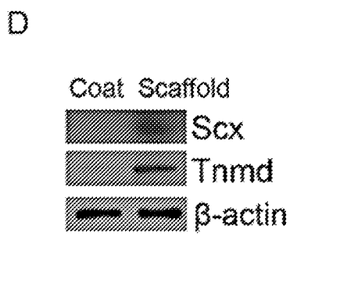

2. MSCs growing on the novel silk scaffold, but not on the silk protein coated surface, express tendon phenotypic markers Scleraxis and Tenomodulin. To determine the tenogenic potential of these MSCs seeded on the silk scaffolds, relative gene expression of Scleraxis (Sex), an early marker of tendon differentiation, was assayed. Sex expression increased from 4 hours to 24 hours post seeding, and began to plateau at 24 hours and maintained the same level until 7 days (FIG. 4A). To test whether the tenocyte differentiation promoted by the silk scaffold was in response to the topography of the silk fibers rather than the silk protein itself, the expression of tenogenic phenotypic-related markers and stem cell markers was analyzed in MSCs seeded onto silk scaffolds compared to MSCs cultured on silk-coated culture dishes. Cells cultured on the silk scaffold had significantly higher expression of Scx and tenomodulin (Tnmd), a late marker of tendon formation, compared to MSCs cultured on silk-coated plates (FIG. 4B), indicating tenogenic differentiation was induced due to the physical properties of the silk fibers but not the chemical components of the silk. Cells seeded on the silk scaffold also expressed significantly reduced nucleostemin (Nst), and octamer-binding transcription factor 4 (Oct4), markers for undifferentiated MSCs, when compared to MSCs grown on the silk coated plates (FIG. 4B). These data suggest that MSCs cultured on silk-coated plates remain largely undifferentiated, while cells cultured on the scaffold were differentiating towards a tenogenic lineage. Furthermore, mRNA expression of chondrogenic markers Sox9 and Col2al were unchanged or undetected, respectively, and mRNA expression of osteogenic markers Runt-related transcription factor 2 (Runx2) and alkaline phosphatase (Alp) were undetected, in MSCs seeded either on a silk coated surface or a silk scaffold (FIG. 4B), which may indicate differentiation specifically towards the tenogenic lineage. Immunocytochemistry (FIG. 4C) and Western blot (FIG. 4D) confirmed a lack of Scx and Tnmd expression in MSCs cultured on silk protein-coated plates while expression of Scx and Tnmd was detected in MSCs grown on the silk scaffold. These results strongly suggest that topography (i.e. the elongated-related physical property) of the silk fibers, but not the silk protein/chemical components, is a determining factor for the tenogenic differentiation of the MSCs in this context.

Figure 5A:
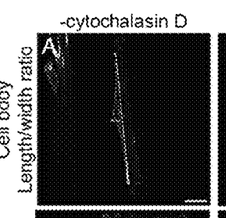
FIG. 5A-5I. Cytochalasin D disrupted actin cytoskeletal arrangement in cells attached to scaffold fibers and abolished the elongated cell body [(5A) vs (5B)] and associated nuclear shape change [(5C) vs (5D)]. (5E) shows the quantitative analysis of the cell body and nuclear shape changes. Cytochalasin D treatment also diminished the expression of tendon phenotypic markers Sex and Tnmd in these cells, as revealed by (5F) immunocytochemistry (blue=DAPI, red=Sex or Tnmd). (5G) Relative mRNA and (5H) western blot of Sex and Tnmd expression with (i) relative mRNA expression of the housekeeping genes Hrptl and Pgkl as an internal control. Data represent at least three independent experiments per assay. *P<0.05 compared to MSCs seeded on a scaffold without cytochalasin D. Scale bar=25 μm.
Figure 5B:
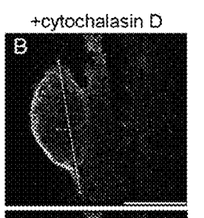
Figure 5C:
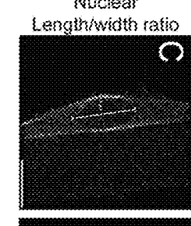
Figure 5D:
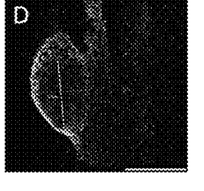
Figure 5E:
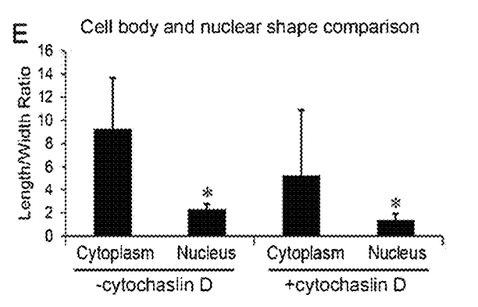
Figure 5F:
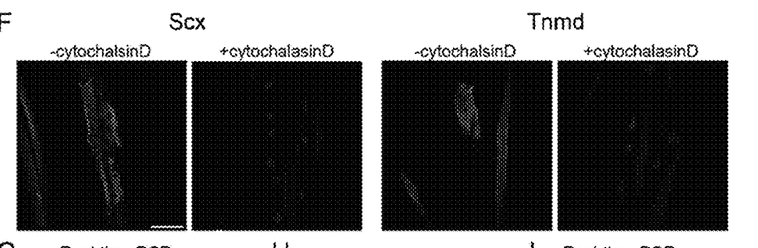
Figures 5G, 5H:
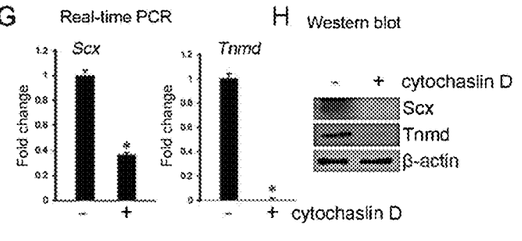

3. Actin polymerization is required for scaffold induced stem cell elongation and expression of tenogenesis markers Scx and Tnmd. To determine the role of cytoskeletal organization in the differentiation of MSCs into tenocytes when MSCs are grown on silk, the effect of cytochalasin D, which inhibits actin polymerization by capping the barbed ends of F-actin polymers was examined on silk-fiber induced MSC teno-differentiation. Differences in cell shape and cell nuclei were quantified by measuring the lengths of the cells that were growing in parallel with the fibers and were compared to the maximal widths of the cells, which were measured perpendicular to the fibers. Cells that were treated with cytochalasin D did not retain an elongated shape, as demonstrated by the smaller length-to-width ratios of their cytoplasms (Fig. SA and SC) and nuclei (FIG. 5B and SD) compared to untreated MSCs. Significant differences were found when quantifying the cytoplasmic (P<0.05) and nuclear (P<0.05) ratios (Fig. SE).

Figure 5I:
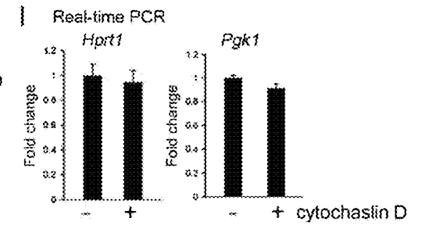

To determine whether actin polymerization in elongated cells is required for tenogenic differentiation, the effect of cytochalasin D was examined on tenogenic marker gene and protein expression in MSCs that were grown on silk scaffolds for 7 days. Compared to untreated controls, cytochalasin D treatment abolished the elongated phenotype of the cells and was found to be associated with a loss of Scx and Tnmd immunocytochemistry staining (Fig. SF), which was confirmed by real-time PCR (FIG. 5G) and western blot (Fig. SH). To determine whether the loss of Scx and Tnmd expression was due to specific effects produced by cytochalasin D on actin polymerization and cell morphology, rather than due to general toxicity related to gene expression, the expression levels of two housekeeping genes, Hypoxanthine-guanine phosphoribosyltransferase 1 (Hprt1) and phosphoglycerate kinase 1 (Pgk1), were analyzed. The results revealed that the expression levels of both genes remained unchanged in the presence of cytochalasin D (FIG. 5I), suggesting that the loss of cell elongation and tenogenic gene expression observed previously was due to changes in actin polymerization.

4. Disruption of stress fiber formation by blocking Rho/Rock Pathway signaling abolished silk scaffold induced MSCs tendon lineage differentiation. To determine the role of stress fibers in mediating silk fiber-induced MSC tenogenic differentiation, the impact of cell signaling on the regulation of stress fiber formation was examined. RhoA and ROCK.II are two small GTPase proteins that have been shown to regulate the actin cytoskeleton during the formation of stress fibers. Accordingly, the following Rho/Rock inhibiting reagents were used to dissect the potential effects of the Rho/Rock pathway on stress fiber formation during the differentiation of MSCs (grown on silk scaffolds) into tenocytes: (1) Latrunculin A, which binds to monomeric G-actin and prevents its polymerization into F-actin and stress fibers; (2) Y-27632 dihydrochloride, which inhibits ROCK activity; and (3) blebbistatin, which selectively inhibits the ATPase function of nonmuscle myosin II.

Figure 6A:
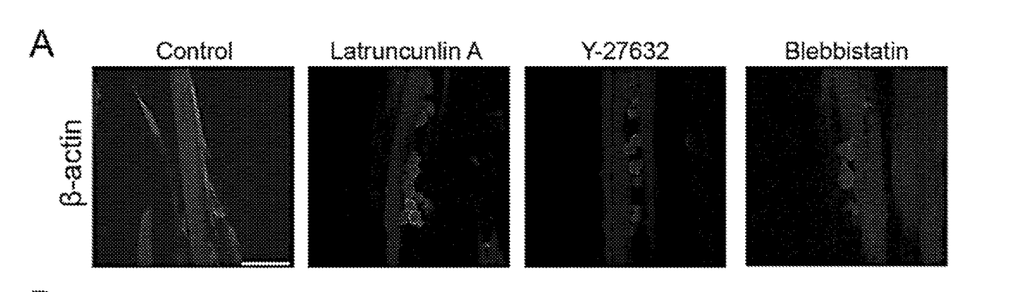
FIG. 6A-6C. Disruption of Rho/Rock Pathway signaling and stress fiber formation are required for tendon lineage determination. (6A) Immunocytochemistry of P-actin in MSCs grown either with no treatment or treated with Latrunculin A, Y-27632 and Blebbistatin for 7 days (blue=DAPI, green=P-actin). *P<0.05 for all treatments. (6B) mRNA expression and protein expression of Sex and mRNA expression of (6C) Coll al and Nfatc4 Nst in MSCs grown on silk scaffolds following treatment with Latrunculin A (LatA), Y-27632 (Y) and Blebbistatin (Bleb) for 24 h. Data represent three independent experiments per assay.
Figure 6B:
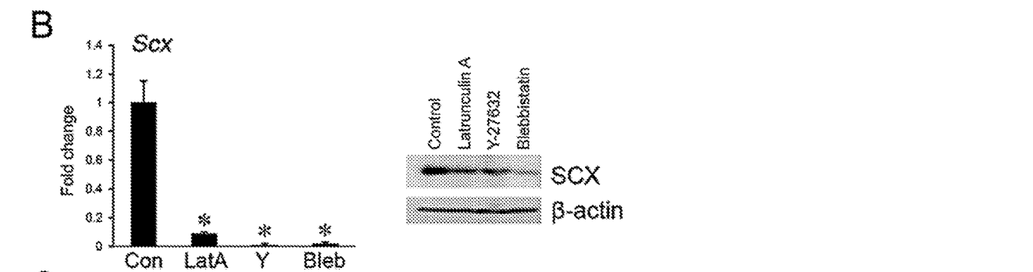
Figure 6C:
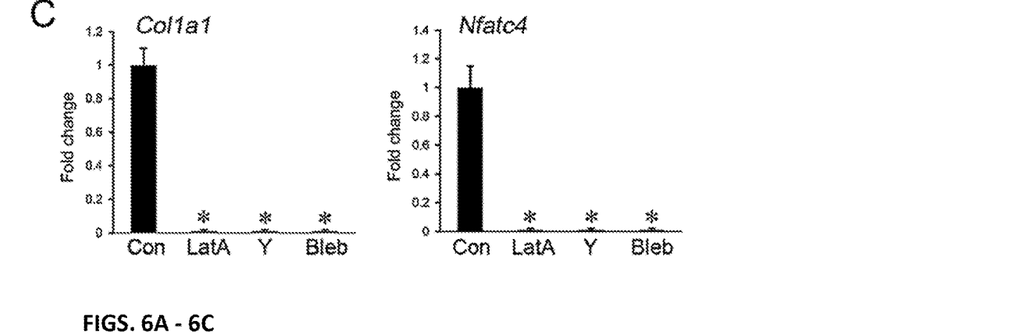

Compared to untreated cells, cells that were exposed to the above treatment conditions lost their elongated phenotype (FIG. 6A). Additionally, the expression levels of Scx mRNAs and SCX proteins were significantly decreased after treatment with Latrunculin A, Y-27632, and blebbistatin (FIG. 6B), which supports that the Rho/Rock pathway plays a role in tenocyte differentiation through its regulation of stress fiber formation. In addition to Scx, the Nfatc4 and Col1 al genes have been suggested to be a part of the regulatory network that is involved in the differentiation of MSCs into tenocytes. Therefore, the expression of Nfatc4 and Col1al following treatment with Latrunculin A, Y-27632, and blebbistatin was also examined. It was found that the expression levels of both Nfatc4 and Col1 al were significantly decreased in response to all three of the treatments (FIG. 6C). Collectively, these findings suggest that the organization of actin stress fibers is a critical determinant of MSC teno-differentiation.

Taken together, these studies show the novel scaffold, via physical but not chemical means, induced the stem cells to elongate. These cell shape changes generated stress fiber formation that led to the generation of mechanical tension which triggered a pathway leading to increased tenogenesis-related gene expression and morphological changes towards tenocyte differentiation.

Figure 7A:
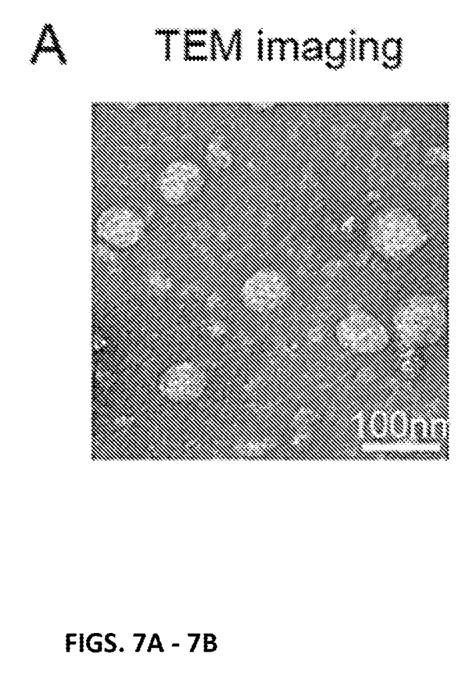
FIG. 7A-7B. Morphology and size distribution of microvesicles grown on a novel silk scaffold detected by TEM (7A) and light scattering (7B), respectively.
Figure 7B:
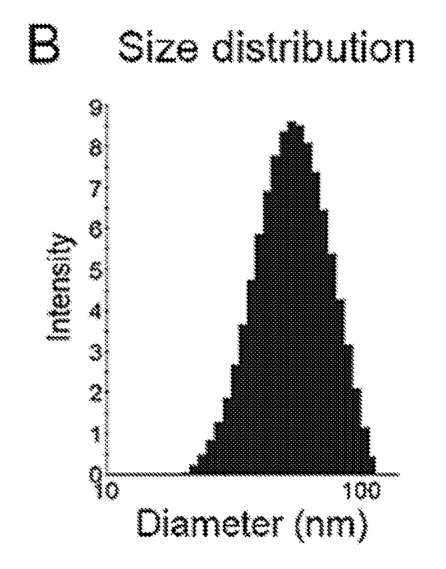

IV. Isolation and characterization of the micro-vesicles derived from stem cells such as tendon stem/progenitor cells (TSPCs) grown on novel scaffold: TSPCs isolated from biceps tissue (48-year-old female) were cultured using the above-mentioned custom-designed silk scaffold in serum-free medium in the presence of 1% penicillin/streptomycin. After 3 days of culture, ⅔ of the conditioned medium was harvested and replaced with fresh medium every other day for 6 days in this study. The micro-vesicles were isolated by differential ultracentrifugation. Briefly, the supernatant was collected after every following step: 1) 300×g, 10 minute; 2) 2000×g, 10 minute; 3) 10,000×g, 30 minute; 4) 100,000×g, 70 min. The resulting pellet was washed in PBS, and subjected to one more centrifugation step (100,000×g, 70 min), which yielded the micro-vesicles. This method is based on a series of centrifugation steps and can be carried out in a custom designed sterile device without expose to the air, therefore allowing to avoid air or chemical contamination. Micro-vesicles isolated from the conditioned medium of MSCs grown on the novel scaffold are termed: "Micro-vesicles-S". Micro-vesicles isolated from the conditioned medium of MSCs grown in 2D culture are termed: "Micro-vesicles-C". Approximately 200 μg of Micro-vesicles-S can be harvested within 48 hours. The Micro-vesicles-S had a diameter from 40-100nm, as revealed by negative staining transmission electron microscopy (TEM) (FIG. 7A) and dynamic light scattering (Dynopro Nanostar) (FIG. 7B).

What is claimed is:

1. A method of treating a damaged tendon in a mammalian subject comprising administering to the subject an amount of microvesicles derived from mammalian mesenchymal stem cells effective to treat a damaged tendon, wherein the mesenchymal stem cells have been cultured on a silk scaffold prior to the microvesicles being derived from the mesenchymal stem cells.

2. The method of claim 1, wherein the microvesicles have been secreted from mesenchymal stem cells.

3. The method of claim 1, wherein the mesenchymal stem cells at P1 to P3 have been cultured on the silk scaffold.

4. The method of claim 1, wherein the mesenchymal stem cells (MSC) are adipose-derived MSC, bone marrow-derived MSC, bursa-derived MSC, or are tendon stem/progenitor cells.

5. The method of claim 1, wherein the mesenchymal stem cells (MSC) are from the same species as the subject.

6. The method of claim 1, wherein the mesenchymal stem cells (MSC) are from the same subject that is being treated.

7. The method of claim 1, wherein the damaged tendon is damaged as a result of a tendinopathy.

8. The method of claim 1, wherein the damaged tendon is damaged as a result of physical injury to the tendon.

9. The method of claim 1, wherein the damaged tendon is a ruptured tendon.

10. The method of claim 1, wherein the amount of microvesicles is administered locally into the tendon.

11. The method of claim 1, wherein the amount of microvesicles is administered by injection.

12. The method of claim 1, wherein the amount of microvesicles has been cryopreserved prior to administration.

13. The method of claim 1, wherein the amount of microvesicles has been cryopreserved below 50° C.

14. A method of enhancing tenogenesis in a damaged tendon in a mammalian subject comprising administering to the subject an amount of microvesicles derived from mammalian mesenchymal stem cells effective to enhance tenogenesis, wherein the mesenchymal stem cells have been cultured on a silk scaffold prior to the microvesicles being derived from the mesenchymal stem cells.

15. The method of claim 14, wherein the mesenchymal stem cells at P1 to P3 have been cultured on the silk scaffold.

* * * * *